United States Patent
Watson et al.

(10) Patent No.: US 9,418,820 B2
(45) Date of Patent: Aug. 16, 2016

(54) COLD PLASMA TREATMENT DEVICES AND ASSOCIATED METHODS

(75) Inventors: Gregory A. Watson, Sanford, FL (US); David J. Jacofsky, Peoria, AZ (US)

(73) Assignee: Plasmology4, Inc., Scottsdale, AZ (US)

( * ) Notice: Subject to any disclaimer, the term of this patent is extended or adjusted under 35 U.S.C. 154(b) by 633 days.

(21) Appl. No.: 13/620,104

(22) Filed: Sep. 14, 2012

(65) Prior Publication Data

US 2013/0072859 A1    Mar. 21, 2013

Related U.S. Application Data

(60) Provisional application No. 61/535,250, filed on Sep. 15, 2011.

(51) Int. Cl.
| H01J 7/24 | (2006.01) |
| H01J 37/32 | (2006.01) |
| A61M 16/06 | (2006.01) |

(Continued)

(52) U.S. Cl.
CPC ............ *H01J 37/321* (2013.01); *A61L 2/00* (2013.01); *A61L 2/0094* (2013.01); *A61L 2/14* (2013.01); *A61M 15/02* (2013.01); *A61M 16/06* (2013.01); *A61M 16/12* (2013.01); *H01J 37/3244* (2013.01); *H01J 37/3266* (2013.01); *H01J 37/32348* (2013.01); *H05H 1/2406* (2013.01); *H05H 1/46* (2013.01); *A61M 2202/025* (2013.01); *A61M 2202/0208* (2013.01); *A61N 1/40* (2013.01); *A61N 1/44* (2013.01); *H05H 2001/2412* (2013.01); *H05H 2001/466* (2013.01); *H05H 2001/4682* (2013.01);

(Continued)

(58) Field of Classification Search
USPC ........................................ 315/111.21–111.91
See application file for complete search history.

(56) References Cited

U.S. PATENT DOCUMENTS

| 2,927,322 A | 3/1960 | Simon et al. |
| 3,432,722 A | 3/1969 | Naydan et al. |

(Continued)

FOREIGN PATENT DOCUMENTS

| DE | 19532105 A1 * | 3/1996 | ............ B05D 3/142 |
| JP | 2006-244938 | 9/2006 | |

(Continued)

OTHER PUBLICATIONS

Dumé, Belle, "Cold Plasmas Destroy Bacteria," article, [online], [retrieved on Jan. 5, 2007], Retrieved from the PhysicsWeb website using Internet <URL:http://physicsweb.org/articles/nevvs7/4/19>.

(Continued)

*Primary Examiner* — Douglas W Owens
*Assistant Examiner* — Srinivas Sathiraju
(74) *Attorney, Agent, or Firm* — Sterne, Kessler, Goldstein & Fox P.L.L.C.

(57) ABSTRACT

A cold plasma helmet application device for delivery of cold plasma benefits to the head of a patient. An appropriate gas is introduced into a helmet receptacle within a containment dome of the helmet. The gas is energized by one or more dielectric barrier devices that receive energy from a pulsed source. The dielectric barrier devices can be configured to match the treatment area. Such a device and method can be used to treat large surface areas treatment sites associated with the head, head trauma, brain cancer, the control of brain swelling with closed head injury or infection, as well as treating male pattern baldness.

17 Claims, 12 Drawing Sheets

(51) Int. Cl.

| | | |
|---|---|---|
| *A61M 16/12* | (2006.01) | |
| *A61M 15/02* | (2006.01) | |
| *H05H 1/24* | (2006.01) | |
| *A61L 2/00* | (2006.01) | |
| *H05H 1/46* | (2006.01) | |
| *A61L 2/14* | (2006.01) | |
| *A61N 1/44* | (2006.01) | |
| *A61N 1/40* | (2006.01) | |

(52) U.S. Cl.
CPC .... *H05H2240/20* (2013.01); *H05H 2245/1225* (2013.01); *H05H 2277/10* (2013.01)

(56) References Cited

U.S. PATENT DOCUMENTS

| | | | |
|---|---|---|---|
| 3,487,414 A | 12/1969 | Booker | |
| 3,735,591 A | 5/1973 | Burkhart | |
| 4,088,926 A | 5/1978 | Fletcher et al. | |
| 4,365,622 A | 12/1982 | Harrison | |
| 4,380,320 A | 4/1983 | Hollstein et al. | |
| 4,422,013 A | 12/1983 | Turchi et al. | |
| 5,079,482 A | 1/1992 | Villecco et al. | |
| 5,216,330 A | 6/1993 | Ahonen | |
| 5,225,740 A | 7/1993 | Ohkawa | |
| 5,304,888 A | 4/1994 | Gesley et al. | |
| 5,698,164 A | 12/1997 | Kishioka et al. | |
| 5,876,663 A | 3/1999 | Laroussi | |
| 5,883,470 A | 3/1999 | Hatakeyama et al. | |
| 5,909,086 A | 6/1999 | Kim et al. | |
| 5,961,772 A | 10/1999 | Selwyn | |
| 5,977,715 A | 11/1999 | Li et al. | |
| 6,096,564 A | 8/2000 | Denes et al. | |
| 6,113,851 A | 9/2000 | Soloshenko et al. | |
| 6,204,605 B1 | 3/2001 | Laroussi et al. | |
| 6,225,593 B1 | 5/2001 | Howieson et al. | |
| 6,228,330 B1 | 5/2001 | Herrmann et al. | |
| 6,262,523 B1 | 7/2001 | Selwyn et al. | |
| 6,441,554 B1 | 8/2002 | Nam et al. | |
| 6,455,014 B1 | 9/2002 | Hammerstrom et al. | |
| 6,611,106 B2 | 8/2003 | Monkhorst et al. | |
| 6,667,007 B1 | 12/2003 | Schmidt | |
| 6,764,658 B2* | 7/2004 | Denes et al. | 422/186.04 |
| 6,956,329 B2 | 10/2005 | Brooks et al. | |
| 6,958,063 B1* | 10/2005 | Soll et al. | 606/41 |
| 7,006,874 B2 | 2/2006 | Knowlton et al. | |
| 7,011,790 B2 | 3/2006 | Ruan et al. | |
| 7,037,468 B2 | 5/2006 | Hammerstrom et al. | |
| 7,081,711 B2 | 7/2006 | Glidden et al. | |
| 7,094,314 B2 | 8/2006 | Kurunczi | |
| 7,192,553 B2 | 3/2007 | Crowe et al. | |
| 7,215,697 B2 | 5/2007 | Hill | |
| 7,271,363 B2 | 9/2007 | Lee et al. | |
| 7,300,436 B2 | 11/2007 | Penny et al. | |
| 7,608,839 B2 | 10/2009 | Coulombe et al. | |
| 7,633,231 B2* | 12/2009 | Watson | 315/111.51 |
| 7,683,342 B2 | 3/2010 | Morfill et al. | |
| 7,691,101 B2 | 4/2010 | Davison et al. | |
| 7,719,200 B2 | 5/2010 | Laroussi | |
| 7,777,151 B2 | 8/2010 | Kuo | |
| 7,785,322 B2 | 8/2010 | Penny et al. | |
| 7,799,290 B2 | 9/2010 | Hammerstrom et al. | |
| 8,263,178 B2* | 9/2012 | Boulos et al. | 427/212 |
| 8,267,884 B1 | 9/2012 | Hicks | |
| 8,294,369 B1 | 10/2012 | Laroussi | |
| 8,460,283 B1 | 6/2013 | Laroussi et al. | |
| 8,928,230 B2* | 1/2015 | Watson et al. | 315/111.91 |
| 2002/0129902 A1 | 9/2002 | Babayan et al. | |
| 2003/0129107 A1* | 7/2003 | Denes et al. | 422/186.21 |
| 2003/0222586 A1 | 12/2003 | Brooks et al. | |
| 2004/0026234 A1* | 2/2004 | Vanden Brande et al. | 204/192.12 |
| 2005/0088101 A1 | 4/2005 | Glidden et al. | |
| 2005/0179395 A1 | 8/2005 | Pai | |
| 2006/0189976 A1 | 8/2006 | Karni et al. | |
| 2008/0145553 A1 | 6/2008 | Boulos et al. | |
| 2008/0159925 A1 | 7/2008 | Shimizu et al. | |
| 2009/0188626 A1 | 7/2009 | Lu et al. | |
| 2010/0133979 A1 | 6/2010 | Lu | |
| 2010/0145253 A1* | 6/2010 | Gutsol et al. | 604/20 |
| 2011/0018444 A1* | 1/2011 | Pouvesle et al. | 315/111.21 |
| 2011/0022043 A1* | 1/2011 | Wandke et al. | 606/41 |
| 2011/0042560 A1 | 2/2011 | Ouyang et al. | |
| 2012/0100524 A1 | 4/2012 | Fridman et al. | |
| 2012/0135390 A1* | 5/2012 | Clyne et al. | 435/1.1 |
| 2012/0187841 A1 | 7/2012 | Kindel et al. | |
| 2012/0259270 A1* | 10/2012 | Wandke et al. | 604/23 |
| 2012/0296265 A1* | 11/2012 | Dobrynin et al. | 604/23 |
| 2013/0015766 A1* | 1/2013 | Taghioskoui et al. | 315/111.41 |
| 2013/0022514 A1 | 1/2013 | Morfill et al. | |
| 2013/0053762 A1* | 2/2013 | Rontal et al. | 604/24 |
| 2013/0064710 A1* | 3/2013 | Jacob | 422/4 |
| 2013/0134878 A1 | 5/2013 | Selwyn | |
| 2013/0199540 A1 | 8/2013 | Buske | |
| 2014/0000810 A1 | 1/2014 | Franklin et al. | |

FOREIGN PATENT DOCUMENTS

| | | |
|---|---|---|
| WO | WO 2005/084569 A1 | 9/2005 |
| WO | WO 2006/116252 | 11/2006 |
| WO | WO 2007/124910 A2 | 11/2007 |
| WO | WO 2010.107722 A1 | 9/2010 |
| WO | WO 2011/055368 A2 | 5/2011 |
| WO | WO 2011/055369 A2 | 5/2011 |
| WO | WO 2011/076193 A1 | 6/2011 |
| WO | WO 2012/106735 A2 | 8/2012 |
| WO | WO 2012/153332 A2 | 11/2012 |
| WO | WO 2013/101673 A1 | 7/2013 |

OTHER PUBLICATIONS

Gould, Phillip and Eyler, Edward, "Ultracold Plasmas Come of Age," article [online], [retrieved on Jan. 5, 2007, Retrieved from the PhysicsWeb website using Internet <URL: http://physicsweb.org/artic les/world/14/3/3>.

Schultz, James, "Cold Plasma Ignites Hot Applications," article, [online], [retrieved on Jan. 5, 2007], Retrieved from the Old Dominion University website using Internet <URL:http://www.odu.edu/ao/instadv/quest/coldplasma.html>.

Lamba, Bikram, "Advent of Cold Plasma," article, [online], [retrieved on Jan. 5, 2007], Retrieved from the PhysOrg.com website using Internet <URL:http/www.physorg.com/printnews.php?newsid=6688>.

Book of Abstracts, 3rd International Conference on Plasma Medicine (ICPM-3), Sep. 19-24, 2010, International Society for Plasma Medicine.

International Search Report issued Aug. 6, 2008 for Appl. No. PCT/US2008/061240, 1 page.

Written Opinion of International Searching Authority issued Aug. 6, 2008 for Appl. No. PCT/US2008/061240, 6 pages.

Extended European Search Report issued Feb. 8, 2012 for European Patent Appl. No. EP08746627.2, 7 pages.

Pointu et al., "Nitrogen Atmospheric Pressure Post Discharges for Surface Biological Decontamination inside Small Diameter Tubes," *Plasma Process. Polym.* 5:559-568, WILEY-VCH Verlag GmbH & Co. KGaA, Weinheim (2008).

Chakravarthy et al., "Cold Spark Discharge Plasma Treatment of Inflammatory Bowel Disease in an Animal Model of Ulcerative Colitis," *Plasma Medicine* (1)1:3-19, Begell House, Inc. (2011).

International Search Report mailed Nov. 30, 2012 for Appl. No. PCT/US2012/55603, 3 pages.

Written Opinion of International Searching Authority mailed Nov. 30, 2012 for Appl. No. PCT/US2012/55603, 3 pages.

English-language abstract for: Ryuichiro et al. JP 2006-244938, Sep. 14, 2006 (listed as FP3), 2 pages.

Fridman et al., "Comparison of Direct and Indirect Effects of Non-Thermal Atmospheric-Pressure Plasma on Bacteria," *Plasma Processl Polym.*, 4, 370-375, 6 pages, WILEY-VCH Verlag GmbH & Co. KGaA, Weinheim (2007).

(56) References Cited

OTHER PUBLICATIONS

Alexander Fridman, "Plasma Chemistry," pp. 263-271, Cambridge University Press, 2008, 9 pages.

O'Connell et al., "The role of the relative voltage and phase for frequency coupling in a dual-frequency capacitively coupled plasma," *Applied Physics Letters*, 93 081502, 3 pages, American Institute of Physics (Aug. 25, 2008).

Nie et al., "A two-dimensional cold atmospheric plasma jet array for uniform treatment of large-area surfaces for plasma medicine," *New Journal of Physics*, 11 115015, 14 pages, IOP Publishing Ltd and Deutsche Physikalische Gesellschaft (2009).

Pompl et al., "The effect of low-temperature plasma on bacteria as observed by repeated AFM imaging," *New Journal of Physics*, 11 115023, 11 pages, IOP Publishing Ltd and Deutsche Physikalische Gesellschaft (Nov. 26, 2009).

Walsh et al., "Three distinct modes in a cold atmospheric pressure plasma jet," *J. Phys. D.: Appl. Phys.* 43 075201, 14 pages, IOP Publishing Ltd (Feb. 3, 2010).

Ricci et al., "The effect of stochastic electrical noise on hard-to-heal wounds," *Journal of Wound Care*, 8 pages, 19:3 Mark Allen Publishing Ltd ( Mar. 2010).

U.S. Appl. No. 61/485,747, filed May 13, 2011, inventor Thomas J. Sheperak, 14 pages.

Liu et al., "Sub-60° C. atmospheric helium-water plasma jets: modes, electron heating and downstream reaction chemistry," *J. Phys. D: Appl. Phys.* 44 345203, 13 pages, IOP Publishing Ltd. (Aug. 11, 2011).

Pei et al., "Inactivation of a 25.5 µm *Enterococcus faecalis* biofilm by a room-temperature, battery-operated, handheld air plasma jet," *J. Phys. D. Appl. Phys.*, 45 165205, 5 pages, IOP Publishing Ltd (Apr. 4, 2012).

Walsh et al., "Chaos in atmospheric-pressure plasma jets," *Plasma Sources Sci. Technol.*, 21 034008, 8 pages, IOP Publishing Ltd (May 2, 2012).

Banu, et al., "Cold Plasma as a Novel Food Processing Technology," *International Journal of Emerging trends in Engineering and Development*, Issue 2, vol. 4, ISSN 2249-6149, pp. 803-818, 16 pages (May 2012).

Dobrynin, et al., "Live Pig Skin Tissue and Wound Toxicity of Cold Plasma Treatment," *Plasma Medicine*, 1(1):93-108, 16 pages, Begell House, Inc. (2011).

Fernández, et al., "The inactivation of *Salmonella* by cold atmosphere plasma treatment," *Food Research International*, 45:2, 678-684, 7 pages, Elsevier Ltd. (Mar. 2012).

Tien, et al., "The Bilayer Lipid Membrane (BLM) Under Electrical Fields," *IEEE Transactions on Dielectrics and Electrical Institute*, 10:5, 717-727, 11 pages (Oct. 2003).

Jayaram, et al.., "Optimization of Electroporation Waveforms for Cell Sterilization," *IEEE Transactions on Industry Applications*, 40:6, 1489-1497, 9 pages (2004).

Fridman, et al., "Use of Non-Thermal Atmospheric Pressure Plasma Discharge for Coagulation and Sterilization of Surface Wounds," *IEEE International Conference on Plasma Science*, Abstract, p. 257, 1 page (Jun. 2005).

Fridman, et al., "Use of Non-Thermal Atmospheric Pressure Plasma Discharge for Coagulation and Sterilization of Surface Wounds," 6 pages (Jun. 2005).

Fridman, et al., "Blood Coagulation and Living Tissue Sterilization by Floating-Electrode Dielectric Barrier Discharge in Air," *Plasma Chem Plasma Process*, 26: 425-442, 18 pages, Springer Science Business Media, Inc. (2006).

Gurol, et al., "Low Temperature Plasma for decontamination of *E. coli* in milk," *International Journal of Food Microbiology*, 157: 1-5, 5 pages, Elsevier B.V. (Jun. 2012).

Lado, et al., "Alternative food-preservation technologies: efficacy and mechanisms," *Microbes and Infection*, 4: 433-440 8 pages, Elsevier SAS (2002).

Leduc, et al., "Cell permeabilization using a non-thermal plasma," *New Journal of Physics*, 11: 115021, 12 pages, IOP Publishing Ltd and Deutsche Physikalische Gesellschaft (2009).

Machado, et al., "Moderate electric fields can inactivate *Escherichia coli* at room temperature," *Journal of Food Engineering*, 96: 520-527, 8 pages, Elsevier Ltd. (2009).

Li, et al., "Optimizing the distance for bacterial treatment using surface micro-discharge plasma," *New Journal of Physics*, 14: 023058, 11 pages, IOP Publishing Ltd and Deutsche Physikalische Gesellschaft (Feb. 2012).

Morfill, et al., "Nosocomial infections—a new approach towards preventive medicine using plasmas," *New Journal of Physics*, 11: 115019, 10 pages, IOP Publishing Ltd and Deutsche Physikalische Gesellschaft (2009).

Nian, et al., "Decontamination of *Salmonella* on Sliced Fruits and Vegetables Surfaces using a Direct-Current, Atmospheric-Pressure Cold Plasma," *IEEE International Conference on Plasma Science*, p. 1, 1 page (Jun. 2011).

Toepfl, et al., "High intensity pulsed electric fields applied for food preservation," *Chemical Engineering and Processing*, 46: 537-546, 10 pages, Elsevier B.V. (2007).

The Supplementary European Search Report mailed Jan. 27, 2015 for Appl. No. PCT/US2012/055603, 7 pages.

\* cited by examiner

COLD PLASMA TREATMENT DEVICES AND ASSOCIATED METHODS

CROSS REFERENCE TO RELATED APPLICATIONS

The present application claims the benefit under 35 U.S.C. § 119(e) of U.S. Provisional Patent Application No. 61/535,250, entitled "Harmonic Cold Plasma Devices and Associated Methods", filed on Sep. 15, 2011, which is hereby expressly incorporated by reference in its entirety.

This application is related to U.S. patent application Ser. No. 13/149,744, filed May 31, 2011, U.S. patent application Ser. No. 12/638,161, filed Dec. 15, 2009, U.S. patent application Ser. No. 12/038,159, filed Feb. 27, 2008, and U.S. Provisional Application No. 60/913,369, filed Apr. 23, 2007, each of which are herein incorporated by reference in their entireties.

BACKGROUND

1. Field of the Art

The present invention relates to devices and methods for creating cold plasmas, and, more particularly, to cold plasma treatment methods and application devices.

2. Background Art

Atmospheric pressure hot plasmas are known to exist in nature. For example, lightning is an example of a DC arc (hot) plasma. Many DC arc plasma applications have been achieved in various manufacturing processes, for example, for use in forming surface coatings. Atmospheric pressure cold plasma processes are also known in the art. Most of the at or near atmospheric pressure cold plasma processes are known to utilize positive to negative electrodes in different configurations, which release free electrons in a noble gas medium.

Devices that use a positive to negative electrode configuration to form a cold plasma from noble gases (helium, argon, etc.) have frequently exhibited electrode degradation and overheating difficulties through continuous device operation. The process conditions for enabling a dense cold plasma electron population without electrode degradation and/or overheating are difficult to achieve.

Different applications of cold plasma devices require different size cold plasma plumes and different dimensional devices to produce those cold plasma plumes. For example, some medical treatments require a large cold plasma plume to treat a large external wound, while other treatments require a small cold plasma device that can be coupled to an elongated medical device that can traverse a small body passageway to reach a small internal treatment site.

BRIEF SUMMARY OF THE INVENTION

Cold plasma may be effective in treating wounds with large surface areas, such as burns, skin graft donor and recipient sites, and tissue flaps, as well as head trauma, melanoma, and other cancers. Additionally, cold plasma may have utility in the control of brain swelling resulting from closed head injury or meningeal infections because of the penetration of the radio frequency (RF) fields generated by the cold plasma device. Cold plasma may also be effective in treating male pattern baldness through a marked increase in localized blood flow to the scalp. The term plasma helmet comes from the overall shape of the plasma applicator. It is generally helmet-shaped, covers the head, and has a series of electrodes (directed toward the target substrate) through which multiple individual plasma discharges are directed.

An embodiment is described of a cold plasma treatment helmet for application to a head having contours. The cold plasma treatment includes a confinement dome, with the confinement dome configured to conform to the contours of the patient's head. The cold plasma treatment helmet also includes a gas injection system having a gas inlet and one or more gas apertures, with the gas inlet configured to receive gas from an external source, and the gas apertures configured to distribute the gas into the confinement dome. The cold plasma treatment helmet also includes one or more DBD devices disposed in the confinement dome, where the one or more DBD devices are coupled to an electrical input port.

An embodiment is also described that includes a method having a step of receiving a biocompatible gas within a confinement dome of a cold plasma treatment helmet, where the biocompatible gas provided via a gas injection system having a gas inlet and one or more gas apertures. The method also includes the step of energizing, by a DBD device, the biocompatible gas to form a cold plasma within the confinement dome. The DBD device is coupled to an electrical input port, where the energy provided via the electrical input port from a cold plasma power supply. The method also includes maintaining the cold plasma within the cold plasma treatment helmet to treat the treatment area.

BRIEF DESCRIPTION OF THE DRAWINGS/FIGURES

Figure 10:
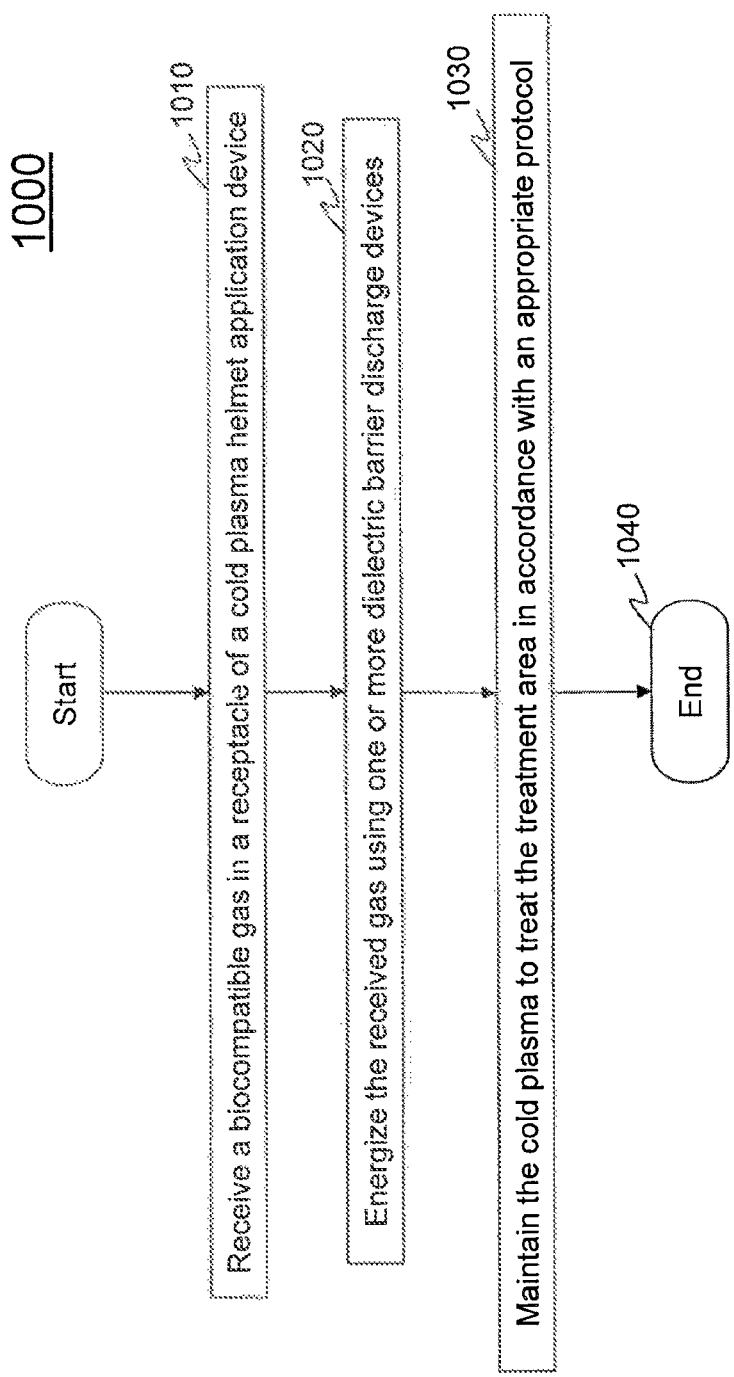

FIG. 10 provides a flowchart of a method of using a cold plasma helmet application device, according to an embodiment of the present invention.

DETAILED DESCRIPTION OF THE INVENTION

Non-thermal atmospheric pressure plasmas have attracted a great deal of enthusiasm and interest by virtue of their provision of plasmas at relatively low gas temperatures. The provision of a plasma at such a temperature is of interest to a variety of applications, including wound healing, anti-infective processes, anti-tumorigenic affects, and various other medical therapies and sterilization.

Cold Plasma Application Device

Figure 1A:
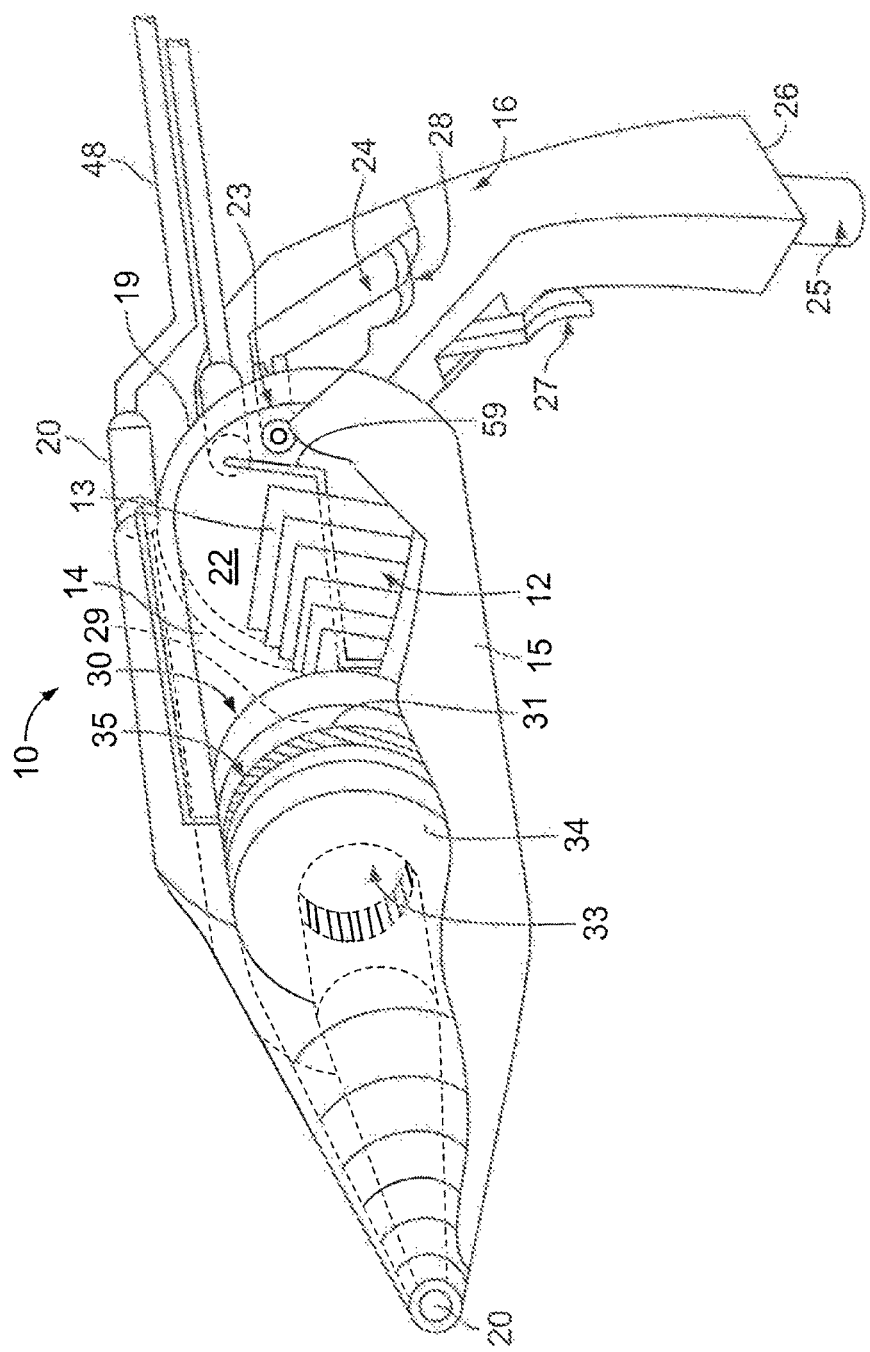
FIGS. 1A and 1B are cutaway views of the hand-held atmospheric harmonic cold plasma device, in accordance with embodiments of the present invention.

To achieve a cold plasma, a cold plasma device typically takes as input a source of appropriate gas and a source of high voltage electrical energy, and outputs a plasma plume. FIG. 1A illustrates such a cold plasma device. Previous work by the inventors in this research area has been described in U.S. Provisional Patent Application No. 60/913,369, U.S. Nonprovisional application Ser. No. 12/038,159 (that has issued as U.S. Pat. No. 7,633,231) and the subsequent continuation applications (collectively "the '369 application family"). The following paragraphs discuss further the subject matter from this application family further, as well as additional developments in this field.

The '369 application family describes a cold plasma device that is supplied with helium gas, connected to a high voltage energy source, and which results in the output of a cold plasma. The temperature of the cold plasma is approximately 65-120 degrees F. (preferably 65-99 degrees F.), and details of the electrode, induction grid and magnet structures are described. The voltage waveforms in the device are illustrated at a typical operating point in '369 application family.

Figure 1B:
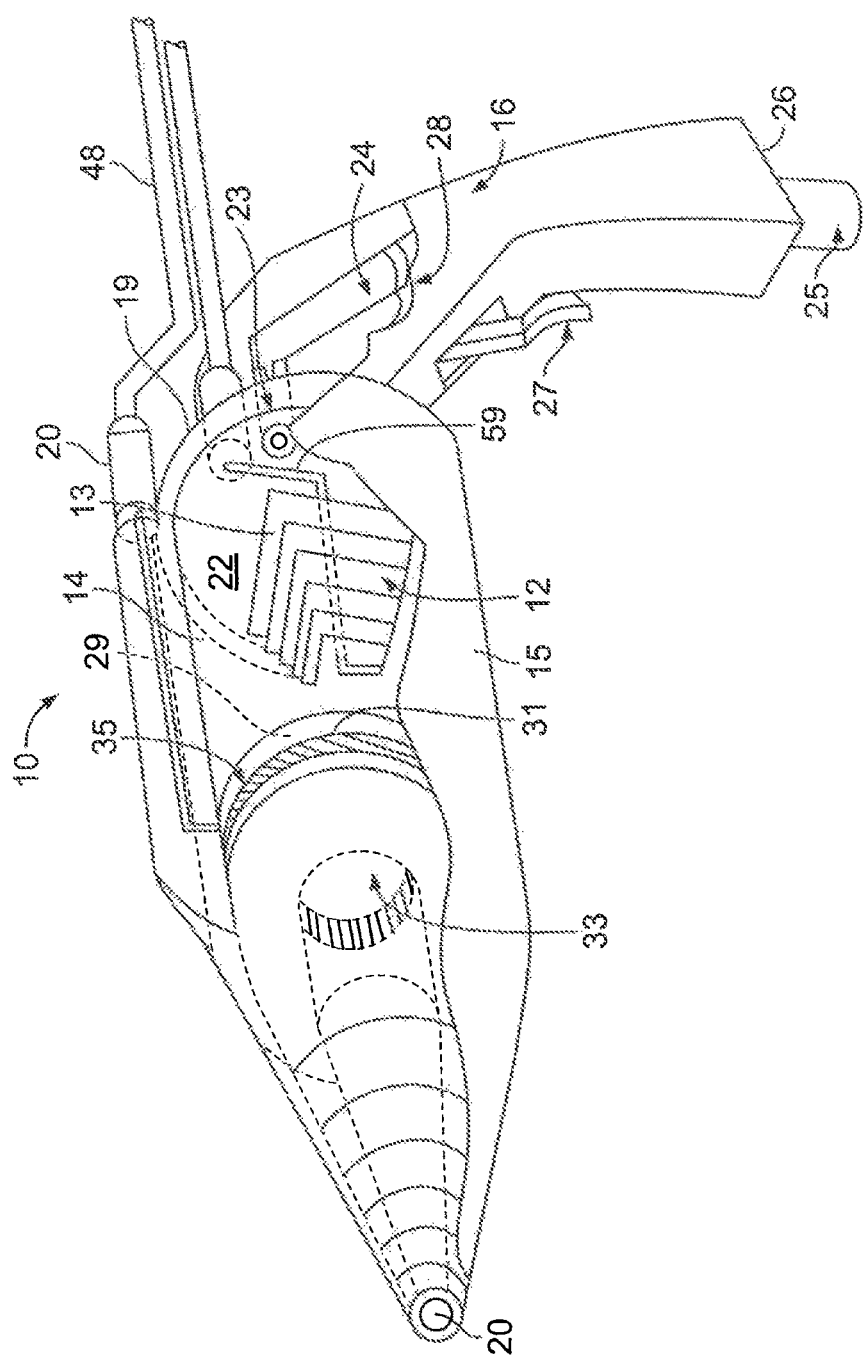
Figure 2A:
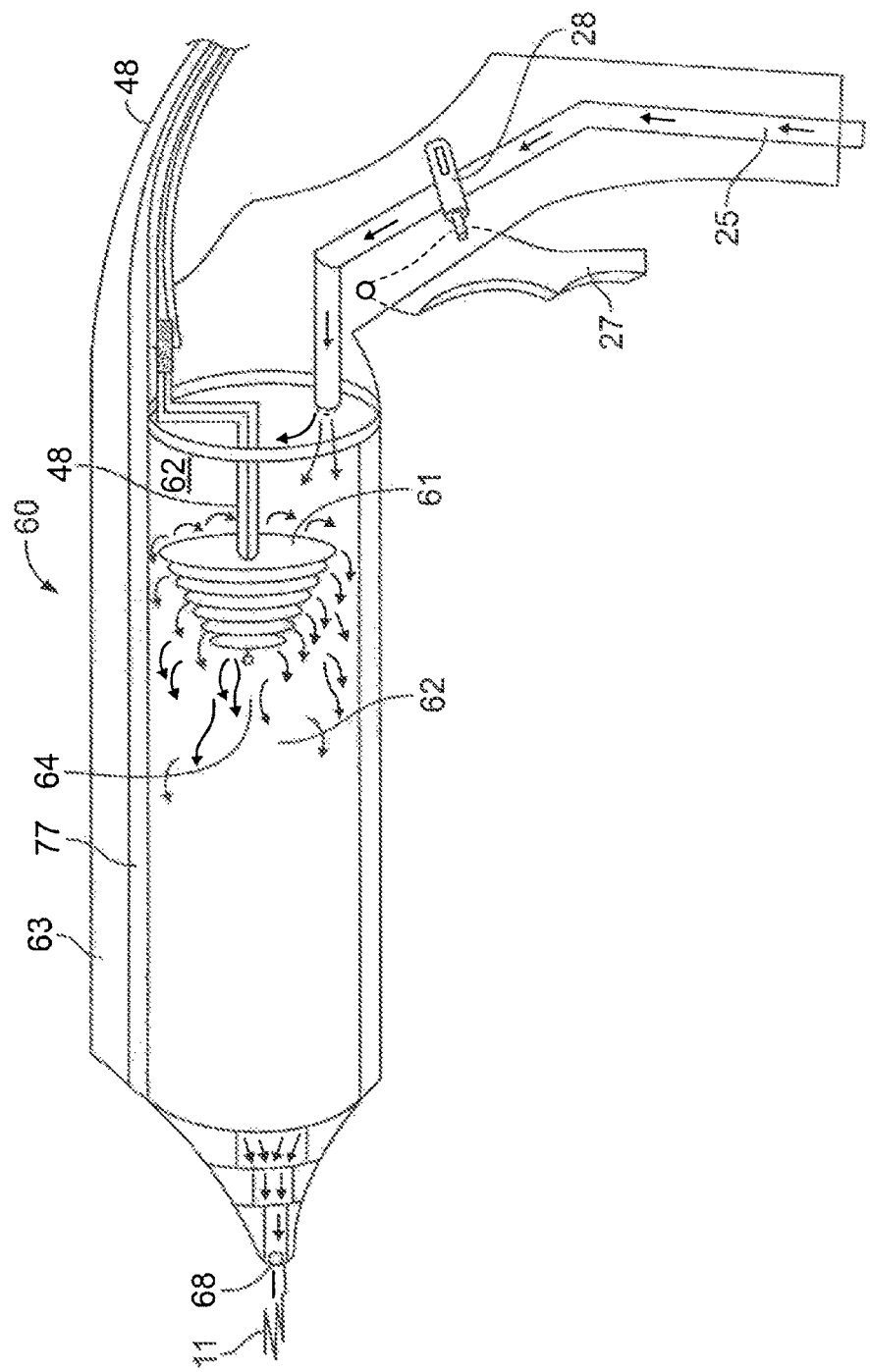
FIGS. 2A and 2B illustrate an embodiment of the cold plasma device without magnets, in accordance with embodiments of the present invention.
Figure 2B:
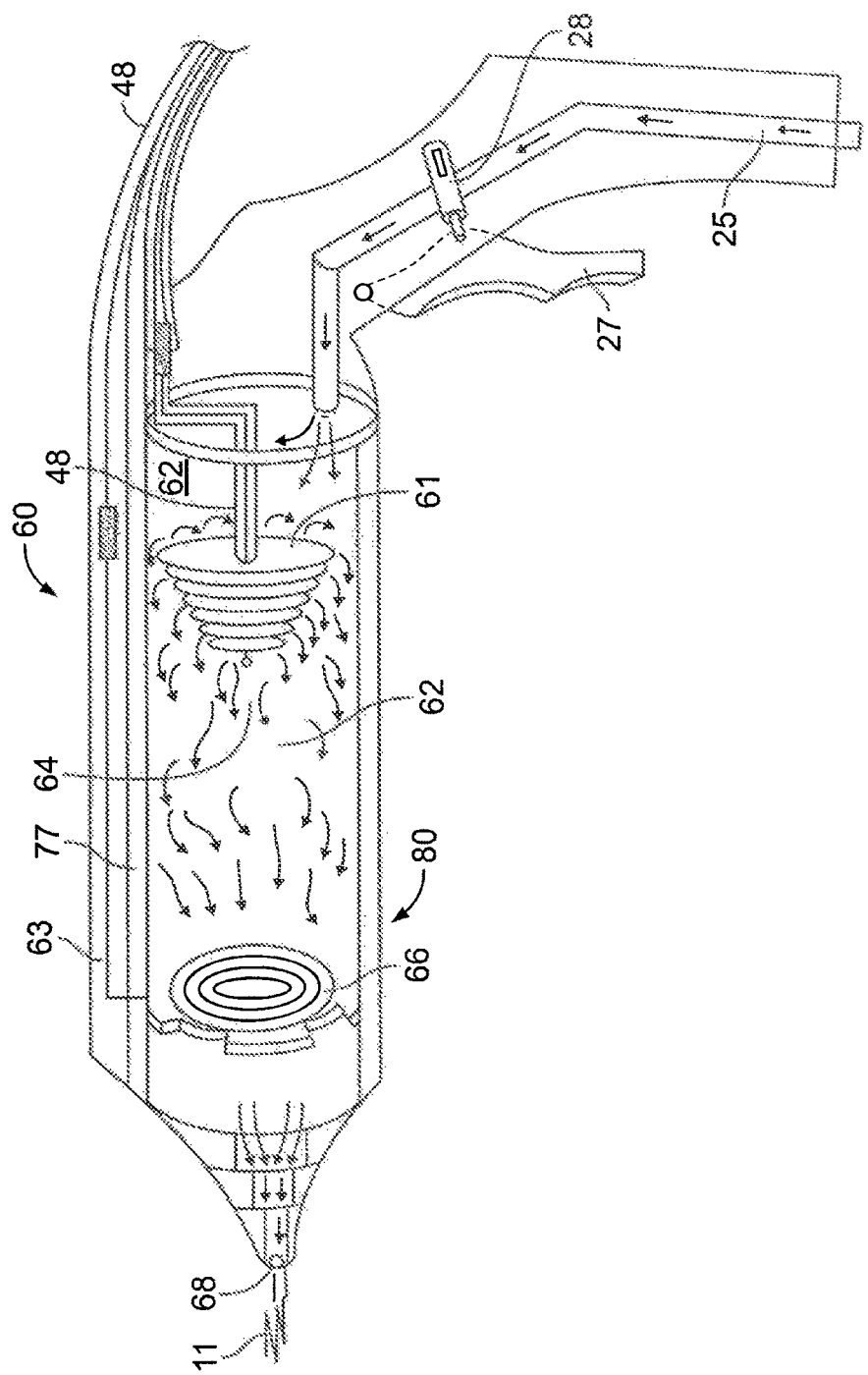

In a further embodiment to that described in the '369 application, plasma is generated using an apparatus without magnets, as illustrated in FIGS. 2A and 2B. In this magnet-free environment, the plasma generated by the action of the electrodes 61 is carried with the fluid flow downstream towards the nozzle 68. FIG. 2A illustrates a magnet-free embodiment in which no induction grid is used. FIG. 2B illustrates a magnet-free embodiment in which induction grid 66 is used. FIG. 1B illustrates the same embodiment as illustrated FIG. 2B, but from a different view. Although these embodiments illustrate the cold plasma is generated from electrode 12, other embodiments do not power the cold plasma device using electrode 12, but instead power the cold plasma device using induction grid 66.

In both a magnet and a magnet-free embodiment, the inductance grid 66 is optional. When inductance grid 66 is present, it provides ionization energy to the gas as the gas passes by. Thus, although the inductance grid 66 is optional, its presence enriches the resulting plasma.

As noted above, the inductance grid 66 is optional. When absent, the plasma will nevertheless transit the cold plasma device and exit at the nozzle 68, although in this case, there will be no additional ionization energy supplied to the gas as it transits the later stage of the cold plasma device.

As noted with respect to other embodiments, magnetic fields can be used in conjunction with the production of cold plasmas. Where present, magnetic fields act, at least at some level, to constrain the plasma and to guide it through the device. In general, electrically charged particles tend to move along magnetic field lines in spiral trajectories. As noted elsewhere, other embodiments can comprise magnets configured and arranged to produce various magnetic field configurations to suit various design considerations. For example, in one embodiment as described in the previously filed '369 application family, a pair of magnets may be configured to give rise to magnetic fields with opposing directions that act to confine the plasma near the inductance grid.

Cold Plasma Unipolar High Voltage Power Supply

The '369 application family also illustrates an embodiment of the unipolar high voltage power supply architecture and components used therein. The circuit architecture is reproduced here as FIG. 3, and this universal power unit provides electrical power for a variety of embodiments described further below. The architecture of this universal power unit includes a low voltage timer, followed by a preamplifier that feeds a lower step-up voltage transformer. The lower step-up voltage transformer in turn feeds a high frequency resonant inductor-capacitor (LC) circuit that is input to an upper step-up voltage transformer. The output of the upper step-up voltage transformer provides the output from the unipolar high voltage power supply.

Figure 3:
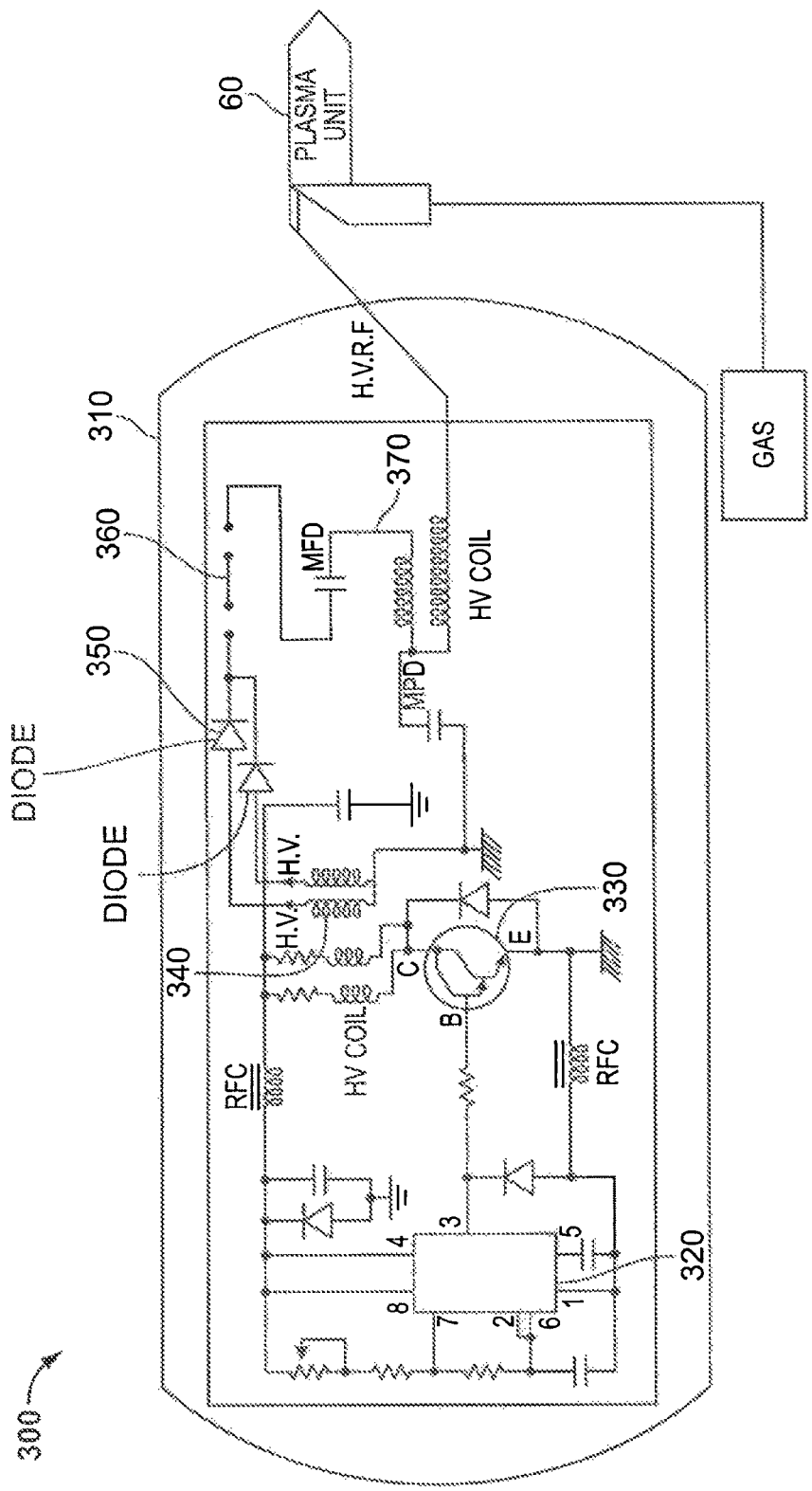
FIG. 3 is an exemplary circuit diagram of the power supply of a cold plasma device, in accordance with embodiments of the present invention.

FIG. 3 also illustrates an exemplary implementation of the unipolar high voltage power supply 310 architecture. In this implementation, a timer integrated circuit such as a 555 timer 320 provides a low voltage pulsed source with a frequency that is tunable over a frequency range centered at approximately 1 kHz. The output of the 555 timer 320 is fed into a preamplifier that is formed from a common emitter bipolar transistor 330 whose load is the primary winding of the lower step-up voltage transformer 340. The collector voltage of the transistor forms the output voltage that is input into the lower step-up voltage transformer. The lower step-up transformer provides a magnification of the voltage to the secondary windings. In turn, the output voltage of the lower step-up voltage transformer is forwarded to a series combination of a high voltage rectifier diode 350, a quenching gap 360 and finally to a series LC resonant circuit 370. As the voltage waveform rises, the rectifier diode conducts, but the quench gap voltage will not have exceeded its breakdown voltage. Accordingly, the quench gap is an open circuit, and therefore the capacitor in the series LC resonant circuit will charge up. Eventually, as the input voltage waveform increases, the voltage across the quench gap exceeds its breakdown voltage, and it arcs over and becomes a short circuit. At this time, the capacitor stops charging and begins to discharge. The energy stored in the capacitor is discharged via the tank circuit formed by the series LC connection.

Continuing to refer to FIG. 3, the inductor also forms the primary winding of the upper step-up voltage transformer 340. Thus, the voltage across the inductor of the LC circuit will resonate at the resonant frequency of the LC circuit 370, and in turn will be further stepped-up at the secondary winding of the upper step-up voltage transformer. The resonant frequency of the LC circuit 370 can be set to in the high kHz-low MHz range. The voltage at the secondary winding of the upper step-up transformer is connected to the output of the power supply unit for delivery to the cold plasma device. The typical output voltage is in the 10-150 kV voltage range. Thus, voltage pulses having a frequency in the high kHz-low MHz range can be generated with an adjustable repetition frequency in the 1 kHz range. The output waveform is shaped similar to the acoustic waveform generated by an impulse such as a bell is struck with a hammer. Here, the impulse is provided when the spark gap (or SCR) fires and produces the voltage pulse which causes the resonant circuits in the primary and secondary sides of the transformer to resonate at their specific resonant frequencies. The resonant frequencies of the primary and the secondary windings are different. As a result, the two signals mix and produce the unique 'harmonic' waveform seen in the transformer output. The net result of the unipolar high voltage power supply is the production of a high voltage waveform with a novel "electrical signature," which when combined with a noble gas or other suitable gas, produces a unique harmonic cold plasma that provides advantageous results in wound healing, bacterial removal and other applications.

The quenching gap 360 is a component of the unipolar high voltage power supply 310. It modulates the push/pull of electrical energy between the capacitance banks, with the resulting generation of electrical energy that is rich in harmonic content. The quenching gap can be accomplished in a number of different ways, including a sealed spark gap and an unsealed spark gap. The sealed spark gap is not adjustable, while unsealed spark gaps can be adjustable. A sealed spark gap can be realized using, for example, a DECI-ARC 3000 V gas tube from Reynolds Industries, Inc. Adjustable spark gaps provide the opportunity to adjust the output of the unipolar high voltage power supply and the intensity of the cold plasma device to which it is connected. In a further embodiment of the present invention that incorporates a sealed (and therefore non-adjustable) spark gap, thereby ensuring a stable plasma intensity.

In an exemplary embodiment of the unipolar high voltage power supply, a 555 timer 320 is used to provide a pulse repetition frequency of approximately 150-600 Hz. As discussed above, the unipolar high voltage power supply produces a series of spark gap discharge pulses based on the pulse repetition frequency. The spark gap discharge pulses have a very narrow pulse width due to the extremely rapid discharge of capacitive stored energy across the spark gap. Initial assessments of the pulse width of the spark gap discharge pulses indicate that the pulse width is approximately 1 nsec. The spark gap discharge pulse train can be described or modeled as a filtered pulse train. In particular, a simple resistor-inductor-capacitor (RLC) filter can be used to model the capacitor, high voltage coil and series resistance of the unipolar high voltage power supply. In one embodiment of the invention, the spark gap discharge pulse train can be modeled as a simple modeled RLC frequency response centered in the range of around 100 MHz. Based on the pulse repetition frequency of 192 Hz, straightforward signal analysis indicates that there would be approximately 2,000,000 individual harmonic components between DC and 400 MHz.

In another embodiment of the unipolar high voltage power supply described above, a 556 timer or any timer circuit can be used in place of the 555 timer 320. In comparison with the 555 timer, the 556 timer provides a wider frequency tuning range that results in greater stability and improved cadence of the unipolar high voltage power supply when used in conjunction with the cold plasma device.

Cold Plasma Dielectric Barrier Device

Figure 4:
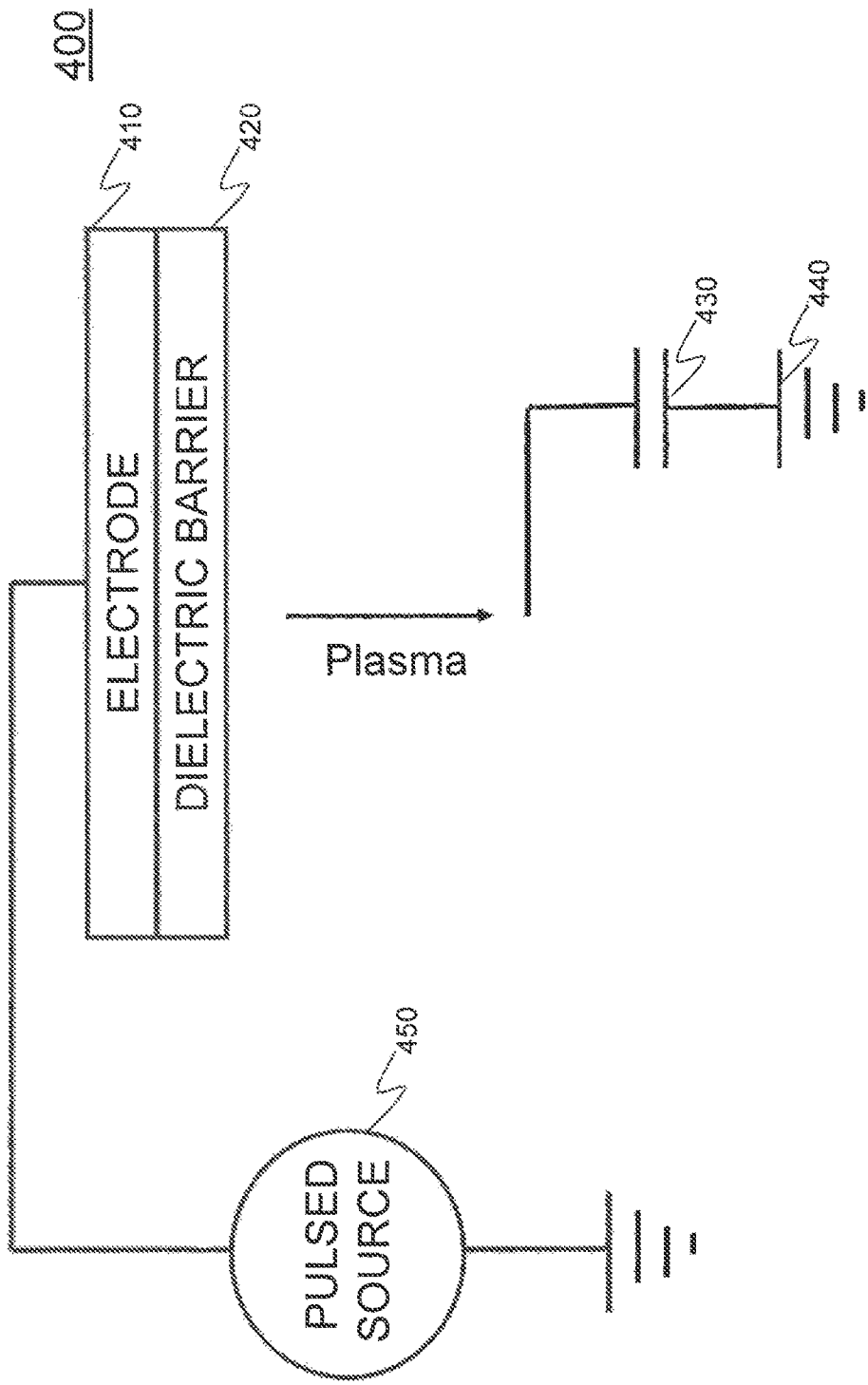
FIG. 4 illustrates the generation of cold plasma resulting from a dielectric barrier device, in accordance with embodiments of the present invention.

Devices, other than the cold plasma device illustrated above in FIG. 1, can also generate cold plasma. For example, cold plasma can also be generated by a dielectric barrier device, which relies on a different process to generate the cold plasma. As FIG. 4 illustrates, a dielectric barrier device (DBD) 400 contains one metal electrode 410 covered by a dielectric layer 420. The electrical return path 430 is formed by the ground 440 that can be provided by the substrate undergoing the cold plasma treatment. Energy for the dielectric barrier device 400 can be provided by a power supply 450, such as that described above and illustrated in FIG. 2. More generally, energy is input to the dielectric barrier device in the form of pulsed electrical voltage to form the plasma discharge. By virtue of the dielectric layer, the discharge is separated from the metal electrode and electrode etching is reduced. The pulsed electrical voltage can be varied in amplitude and frequency to achieve varying regimes of operation.

In exemplary embodiments, the DBD principle is used to provide devices and methods for the application of cold plasma to one or more treatment areas on the head of a patient. The cold plasma application device has a helmet form, which provides a confinement dome to which an appropriate gas (e.g., helium, oxygen, nitrogen and the like, including gas combinations) is received, energized to form a cold plasma and provided in close proximity to the desired treatment area, but prevented from reaching unintended areas. Due to the close proximity, the energy of the cold plasma may be buffered in order to provide a lower energy cold plasma. In certain embodiments, the cold plasma helmet application device has support points on the helmet of the patient to ensure that the confinement dome suitably mirrors the individual contours of the head of the particular patient. In the cold plasma helmet application device, the plasma penetrates to the scalp of the patient. The gas is injected and passes through the DBD devices, which energize the gas to form a cold plasma. The cold plasma passes through to the scalp, which uses the scalp as a ground. In certain embodiments, it is the electromagnetic fields associated with the cold plasma rather than direct cold plasma contact that can provide a therapeutic effect on the treatment area, particularly on deeper tissues.

Cold Plasma Helmet Treatment Device

Figure 5:
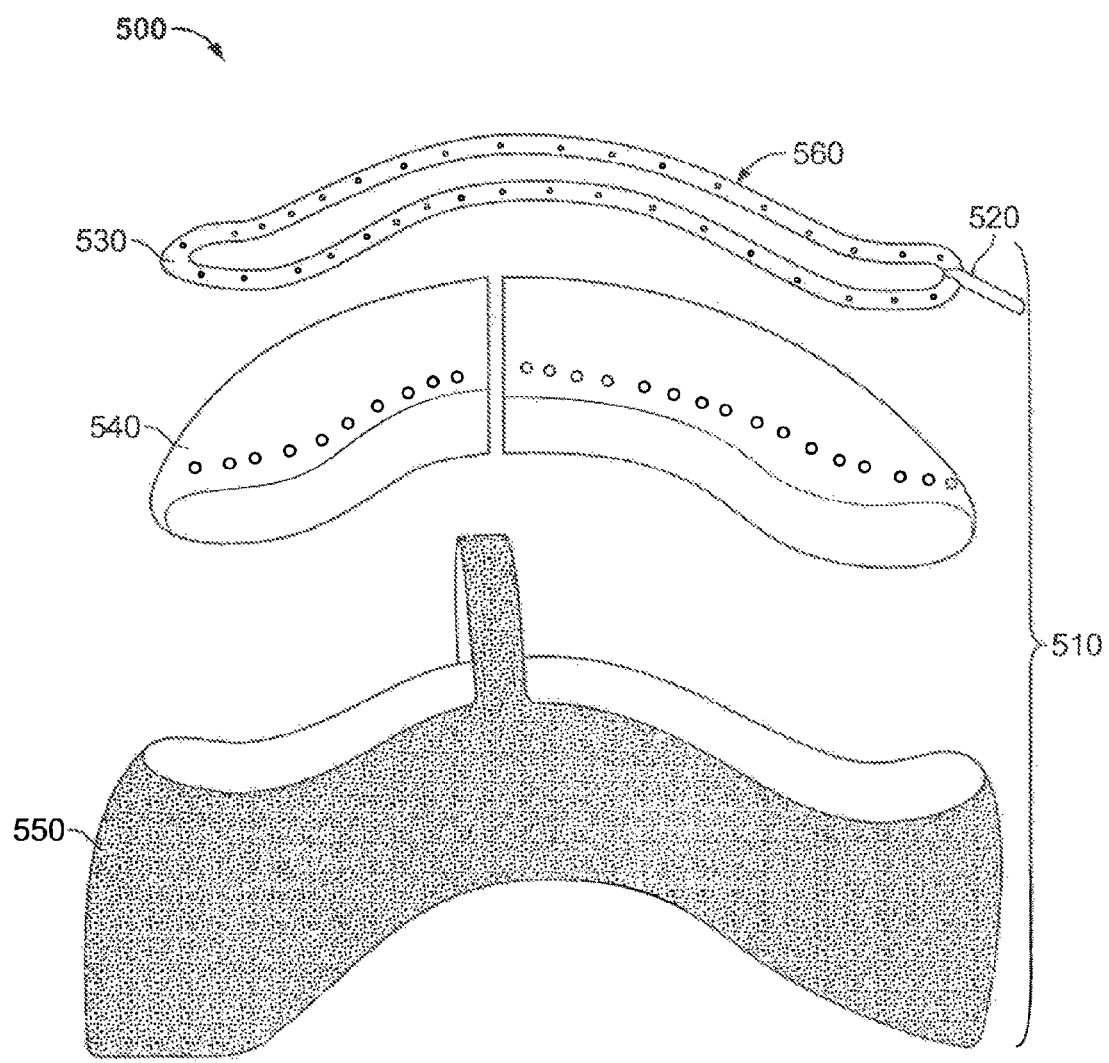
FIG. 5 illustrates device cold plasma application device, in accordance with an embodiment of the present invention.

Cold plasma may be effective in treating wounds with large surface areas, such as burns, skin graft donor and recipient sites, and tissue flaps, as well as head trauma, brain infections, demyelinating diseases, Parkinson's disease, Alzheimer's disease, brain cancers, melanoma, and other cancers. Non-thermal plasma may have utility in the control of brain swelling resulting from closed head injury or infection because of the penetration of the radio frequency (RF) fields generated by the cold plasma device. Cold plasma may also be effective in treating male pattern baldness through a marked increase in localized blood flow to the scalp. In addition, applications to which cold plasma treatments can be applied include the treatment of head wounds, hair growth and scalp treatments that benefit from a diminution of scalp bacteria In an embodiment, a device and method are provided for the application of cold plasma to a treatment area on the head of a patient. Such a device may be referred to as a cold plasma helmet application device, where the term cold plasma helmet comes from the overall shape of the plasma applicator. FIG. 5 illustrates an exemplary embodiment of such a cold plasma helmet application device 500. Cold plasma helmet application device is generally helmet-shaped, covers the head, and has a series of dielectric barrier discharge (DBD) electrodes (directed toward the head of the patient) through which multiple individual plasma discharges are directed. More specifically, in an exemplary embodiment, the cold plasma helmet application device 500 has a confinement dome 510 to which an appropriate biocompatible gas (e.g., helium, oxygen, nitrogen or their combination) is received via gas inlet 520. Gas is then distributed to helmet gas receptacle 550 via gas injection system 560 that has one or more apertures 530. In an embodiment of gas injection system 560, a vinyl tubing configuration is shown. Other means of gas distribution fall within the scope of embodiments of the present invention. The gas is energized to form a non-thermal plasma using one or more dielectric discharge barrier devices (an embodiment shown in FIG. 6) that are located in dome layer 540. Dome layer 540 is made of any suitable dielectric material. Dome layer 540 also has apertures that permit the flow of gas through dome layer 540. The resulting cold plasma passes through to the desired treatment area (e.g., the scalp) on the head of the patient, but prevented from reaching unintended areas (e.g., other parts of the head that are not undergoing treatment). Due to the close proximity, the energy of the cold plasma can be buffered in order to provide a lower energy cold plasma. The cold plasma helmet application device 500 has support points on the head of the patient to ensure that the confinement dome 510 provides the appropriate functionality for the individual contours of the head of the particular patient. The confinement dome 510 can be made using moldable material that prevents penetration by the plasma. Such moldable materials include polyethylene, silicone, or room temperature vulcanizing (RTV) products for example.

Figure 6:
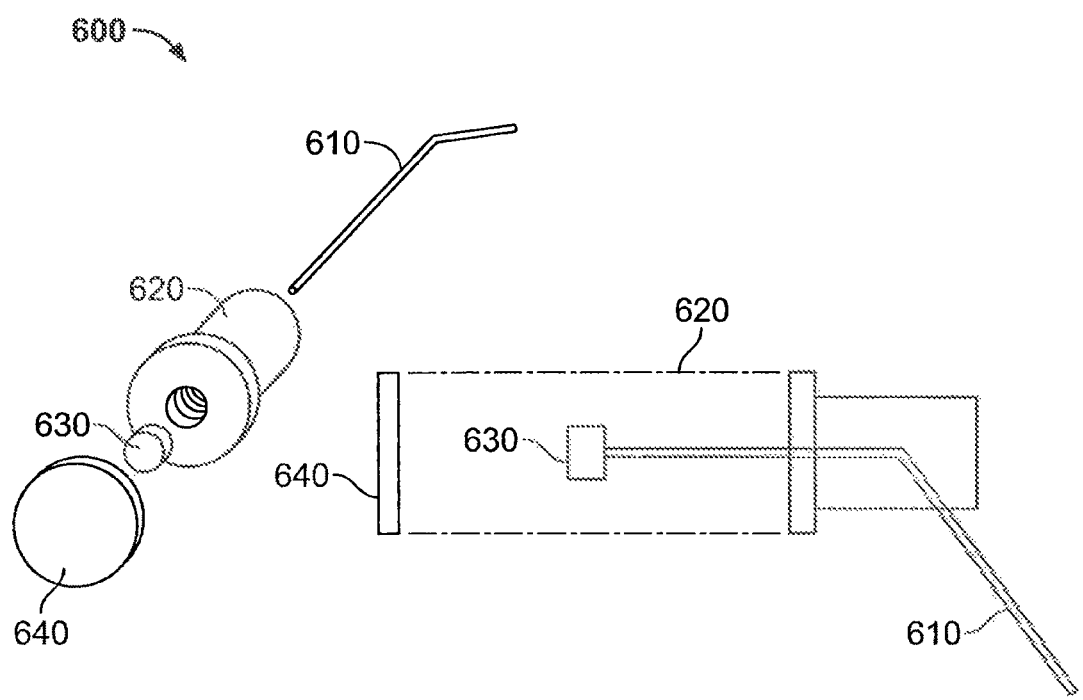
FIG. 6 illustrates a dielectric barrier discharge device, in accordance with an embodiment of the present invention.

FIG. 6 illustrates an exemplary dielectric barrier discharge (DBD) device 600. Dielectric barrier discharge (DBD) device 600 includes electrode 630 within a module housing 620. Electrode 630 is covered by a dielectric disk 640. Electrode 630 is connected to a power supply cable 610. In an embodiment of DBD device 600, dielectric disk 640 is positioned at one end of module housing 620, while the power supply cable 610 enters the module housing 620 at the other end. Although FIG. 6 illustrates module housing 620 is cylindrical in shape, any shape falls within the scope of the present invention.

Figure 7:
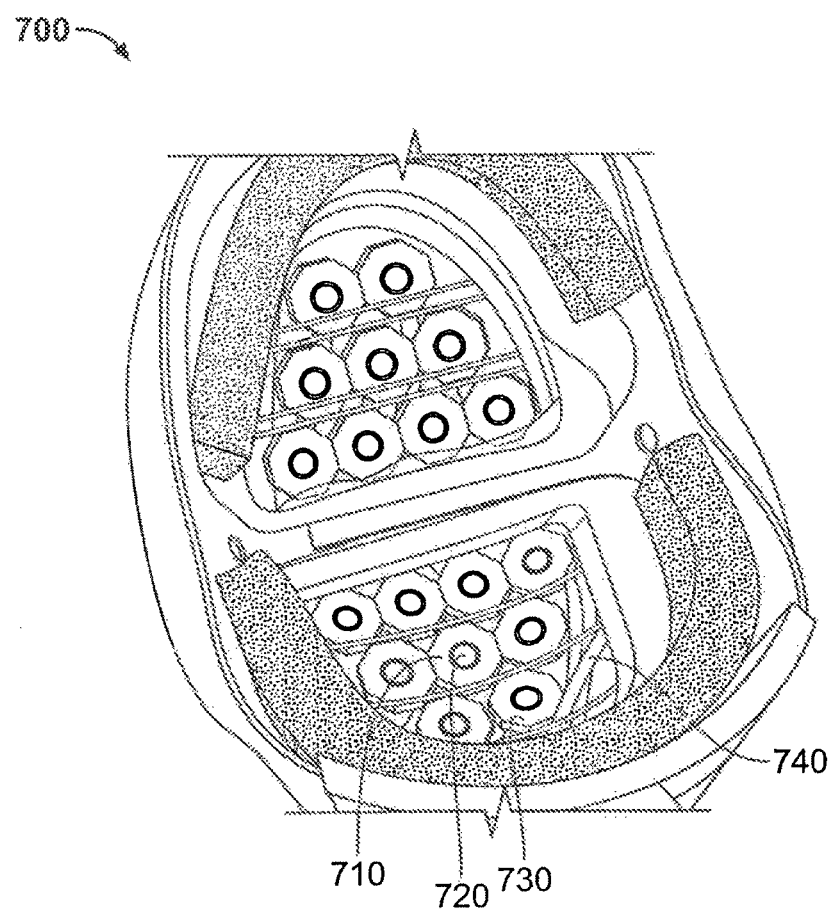
FIG. 7 illustrates an underside view of a cold plasma helmet application device, in accordance with an embodiment of the present invention.

FIG. 7 illustrates the underside of an exemplary cold plasma helmet application device 700. In cold plasma helmet application device 700, a number of DBD devices 710 are distributed throughout the inside, with the electrodes 720 of the DBD devices 710 being covered by transparent silicon dioxide disks 730. Wire grid 740 is also shown that connects the individual DBD devices 710 to a port (not shown) that provides connectivity to an appropriate external cold plasma power supply. In this embodiment, electrodes 720 can be made from any suitable metallic material, such as brass and may be plated with one or more layers of exotic metals such as nickel, silver and/or gold.

Figure 8:
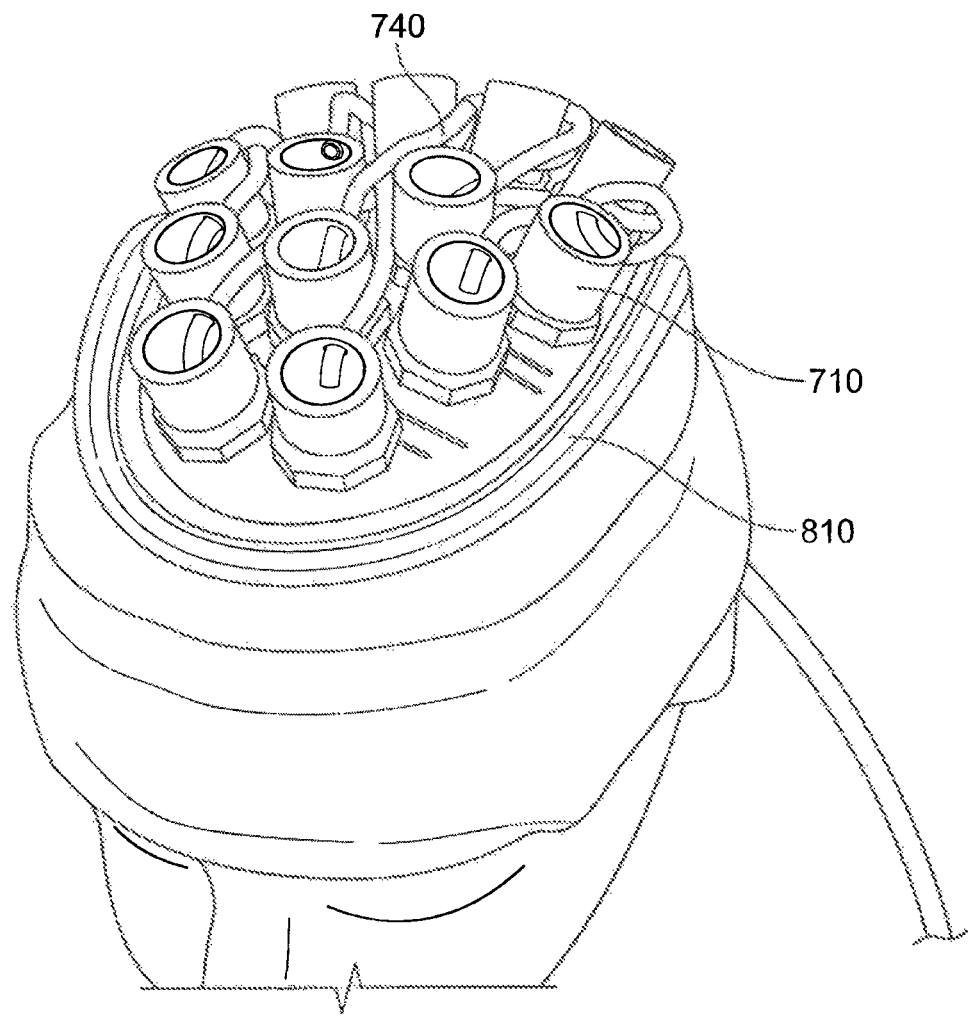
FIG. 8 illustrates a top-side view of a cold plasma helmet application device, in accordance with an embodiment of the present invention.

FIG. 8 illustrates the top-side of exemplary cold plasma helmet application device 700. The DBD devices 710 are distributed throughout the inside, with the wire grid 740 also visible in this view. Gas injection system 810 is shown in this view.

Figure 9:
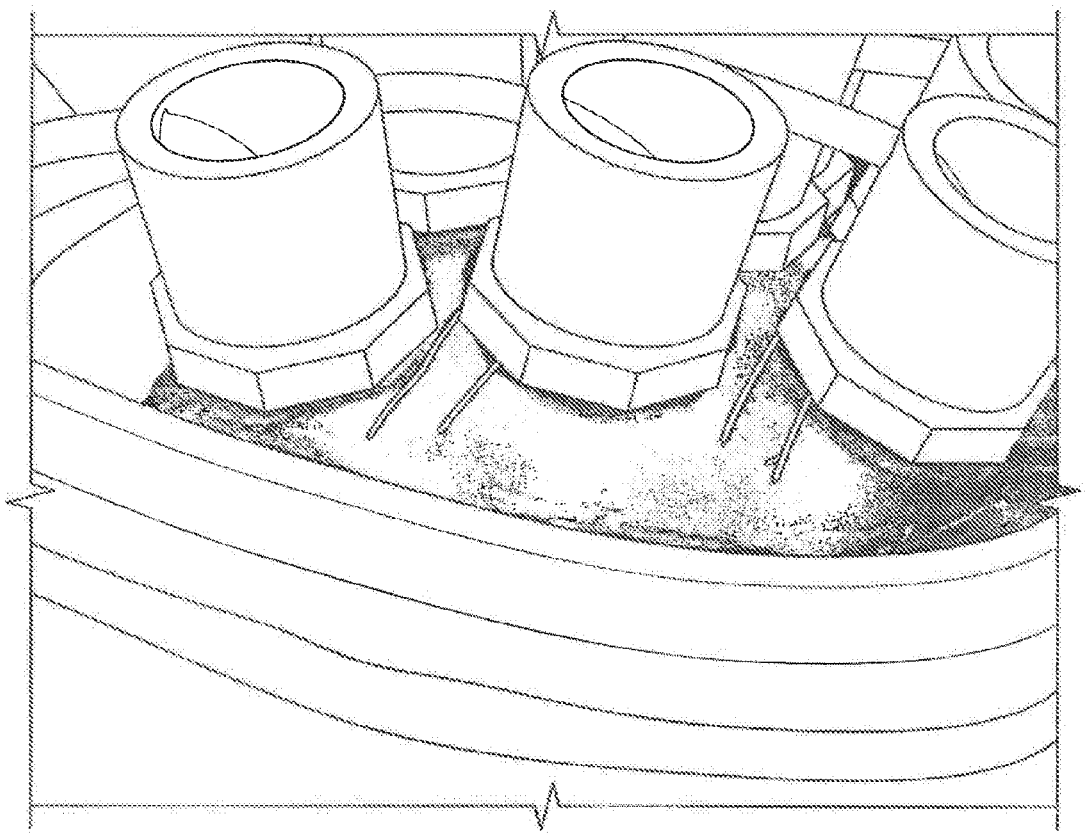
FIG. 9 illustrates an exemplary cold plasma helmet application device, in accordance with an embodiment of the present invention.

FIG. 9 illustrates an exemplary cold plasma helmet application device in operation, with the visible non-thermal plasma shown. The layout of DBD devices in the cold plasma helmet application device can lead to overlap of the plasma fields in the treatment area of the head of the patient involved.

The cold plasma helmet arrangement combines some aspects of dielectric barrier discharge (DBD) plasmas with atmospheric pressure plasma jets (APPJ) to create a unique effect. DBD plasmas are generally created in a non-equilibrium mode by passing electrical discharges over a small distance through ambient air. The electrode shape for a DBD plasma is generally demonstrated as a flat disk shape, or any shape of essentially two dimensions. APPJ may be generated as equilibrium or non-equilibrium plasmas but involve direct contact between the plasma energy source (electrode array) and the feed gas, generally in three dimensions (e.g., pin-in-tube electrode, cylindrical electrode). In this embodiment, a flat, plate-like, two-dimensional electrode is separated from a feed gas by a dielectric barrier, thus separating the electrode from the gas yet causing an ionized gas stream to exit the device in a controlled manner. This provides for a broad surface of plasma generation with the benefit of feed gas control allowing for subsequent optimization of the plasma chemistry and biological effects. The harmonic cold plasma power source design allows for this high level of ionization without substantial temperature rise. The combined effect of multiple simultaneous RF waveforms increases the ionization level of the gas while maintaining low overall gas temperatures. This device can be powered by the same power supply unit as the '369 patent family, or any other suitable cold plasma power supply unit.

In further embodiments of the present invention, the layout of the DBD devices can be reconfigurable to address different treatment areas of the head of a patient. Re-configurability can be achieved by enabling each of the individual DBD devices be easily removable, as required. In an alternative embodiment, the electrical connectivity of the individual DBD devices can be adjusted so that particular DBD devices are activated, while others are not energized with electrical power. In a further embodiment, the overall voltage, frequency content, and duty cycle supplied to the DBD devices from the external cold plasma supply can be adjusted in accordance with a treatment protocol strategy.

Cold Plasma Helmet Method

FIG. 10 provides a flowchart of an exemplary method 1000 use of a cold plasma helmet application device, according to an embodiment of the present invention.

The process begins at step 1010. In step 1010, a biocompatible gas is received in a receptacle of the cold plasma helmet application device.

In step 1020, a biocompatible gas is energized to form a cold plasma within a cold plasma helmet application device, the cold plasma helmet application device having a contour conforming to a head of a patient that includes a treatment area. The biocompatible gas is energized by one or more DBD devices that are disposed within the cold plasma helmet application device in close proximity to the treatment area.

In step 1030, the cold plasma is maintained within the cold plasma helmet application device to treat the treatment area in accordance with an appropriate protocol.

At step 1040, method 1000 ends.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A cold plasma treatment helmet for application to a head having contours, comprising:
   a confinement dome configured to conform to the contours of the head;
   a gas injection system having a gas inlet and one or more gas apertures, the gas inlet configured to receive gas from an external source, and the one or more gas apertures configured to distribute the gas into the confinement dome; and
   one or more dielectric barrier discharge (DBD) devices disposed in the confinement dome, wherein the one or more DBD devices are coupled to an electrical input port, and wherein the coupling between the one or more DBD devices and the electrical input port includes individual switches for each DBD device.

2. The cold plasma treatment helmet of claim 1, wherein the one or more DBD devices each comprise:
   a housing;
   an electrode disposed internally to the housing, wherein the electrode is coupled to a power supply cable;
   a dielectric disk formed over the electrode.

3. The cold plasma treatment helmet of claim 2, wherein the housing is cylindrical.

4. The cold plasma treatment helmet of claim 2, wherein the dielectric disk comprises silicon dioxide.

5. The cold plasma treatment helmet of claim 2, wherein the electrode comprises metallic material.

6. The cold plasma treatment helmet of claim 1, wherein the gas comprises a biocompatible gas.

7. The cold plasma treatment helmet of claim 1, wherein the gas comprises helium.

8. The cold plasma treatment helmet of claim 1, wherein the one or more DBD devices are disposed in a layout to thereby provide overlapping fields when operating.

9. The cold plasma treatment helmet of claim 1, wherein the one or more DBD devices are individually removable.

10. A method comprising:
    receiving a biocompatible gas within a confinement dome of a cold plasma treatment helmet, the biocompatible gas provided via a gas injection system having a gas inlet and one or more gas apertures;
    energizing, by a dielectric barrier discharge (DBD) device, the biocompatible gas to form a cold plasma within a receptacle of the confinement dome, the DBD device being coupled to an electrical input port, the energy provided via the electrical input port from a cold plasma power supply; and wherein energizing by the DBD device includes closing a switch between the DBD device and the electrical input port; and
    maintaining the cold plasma within the cold plasma treatment helmet to treat a treatment area.

11. The method of claim 10, wherein the energizing by a DBD device comprises using an electrode with a dielectric disk formed over the electrode, the electrode disposed internally to a housing of the DBD device and coupled to the electrical input port and the cold plasma power supply.

12. The method of claim 11, wherein the housing is cylindrical.

13. The method of claim 11, wherein the dielectric disk comprises silicon dioxide.

14. The method of claim 11, wherein the electrode comprises metallic material.

15. The method of claim 10, wherein the biocompatible gas comprises helium.

16. The method of claim 10, wherein the energizing by a DBD device includes energizing by two or more DBD devices that are disposed in a layout to thereby provide overlapping fields.

17. The method of claim 10, further comprising:
    inserting an individually removable DBD device before energizing the individually removable DBD device.

* * * * *